United States Patent
Ahn et al.

(10) Patent No.: US 9,747,701 B2
(45) Date of Patent: Aug. 29, 2017

(54) SYSTEMS AND METHODS FOR EMISSION TOMOGRAPHY QUANTITATION

(71) Applicant: General Electric Company, Schenectady, NY (US)

(72) Inventors: Sangtae Ahn, Guiderland, NY (US); Ravindra Mohan Manjeshwar, Glenville, NY (US); Floribertus P M Heukensfeldt Jansen, Ballston Lake, NY (US); Steven Gerard Ross, Pewaukee, WI (US)

(73) Assignee: General Electric Company, Niskayuna, NY (US)

( * ) Notice: Subject to any disclaimer, the term of this patent is extended or adjusted under 35 U.S.C. 154(b) by 70 days.

(21) Appl. No.: 14/831,568

(22) Filed: Aug. 20, 2015

(65) Prior Publication Data

US 2017/0053423 A1 Feb. 23, 2017

(51) Int. Cl.
*G06K 9/00* (2006.01)
*G06T 11/00* (2006.01)
*G06T 7/00* (2017.01)
*A61B 6/03* (2006.01)
*A61B 6/00* (2006.01)

(52) U.S. Cl.
CPC ............ *G06T 11/003* (2013.01); *A61B 6/037* (2013.01); *A61B 6/5217* (2013.01); *G06T 7/0042* (2013.01); *A61B 6/469* (2013.01); *G06T 2207/10104* (2013.01); *G06T 2207/20104* (2013.01); *G06T 2210/41* (2013.01)

(58) Field of Classification Search
CPC .................................................. G06T 7/0042
See application file for complete search history.

(56) References Cited

U.S. PATENT DOCUMENTS

| 7,039,227 B2 | 5/2006 | Tanaka et al. |
| 8,340,373 B2 | 12/2012 | Claus et al. |
| 8,476,593 B2 | 7/2013 | Degenhardt et al. |

(Continued)

OTHER PUBLICATIONS

Jeffrey A. Fessler and W. Leslie Rogers; Spatial Resolution Properties of Penalized-Likelihood Image Reconstruction: Space-Invariant Tomographs; Sep. 1996; pp. 1346-1358; vol. 5 No. 9, IEEE Transactions on Image Processing.

Jeffrey A. Fessler; Mean and Variance of Implicitly Defined Biased Estimators (Such as Penalized Maximum Likelihood): Applications to Tomography: Mar. 1996; pp. 493-506; vol. 5 No. 3, IEEE Transactions on Image Processing.

(Continued)

*Primary Examiner* — Oneal R Mistry
(74) *Attorney, Agent, or Firm* — Nitin N. Joshi

(57) ABSTRACT

A method includes acquiring scan data for an object to be imaged using an imaging scanner. The method also includes reconstructing a display image using the scan data. Further, the method includes determining one or more aspects of a quantitation imaging algorithm for generating a quantitation image, wherein the one or more aspects of the quantitation imaging algorithm are selected to optimize a quantitation figure of merit for lesion quantitation. The method also includes reconstructing a quantitation image using the scan data and the quantitation imaging algorithm; displaying, on a display device, the display image; determining a region of interest in the display image; determining, for the region of interest, a lesion quantitation value using a corresponding region of interest of the quantitation image; and displaying, on the display device, the lesion quantitation value.

20 Claims, 5 Drawing Sheets

(56) References Cited

U.S. PATENT DOCUMENTS

| | | | |
|---|---|---|---|
| 8,494,244 B2 | 7/2013 | Dutta et al. | |
| 8,634,624 B2 | 1/2014 | Bendriem et al. | |
| 2009/0202035 A1* | 8/2009 | Tsukagoshi | A61B 6/032 378/8 |
| 2012/0230470 A1* | 9/2012 | Bertram | A61B 6/032 378/98.5 |
| 2012/0271840 A1 | 10/2012 | Vosniak et al. | |
| 2013/0105699 A1* | 5/2013 | Asma | A61B 6/037 250/363.03 |
| 2013/0343625 A1 | 12/2013 | Samsonov et al. | |
| 2014/0126794 A1 | 5/2014 | Ahn et al. | |
| 2015/0332456 A1* | 11/2015 | Matsuura | A61B 6/037 382/131 |
| 2016/0203599 A1* | 7/2016 | Gillies | A61B 6/463 382/132 |
| 2016/0310761 A1* | 10/2016 | Li | A61N 5/1038 |
| 2016/0364862 A1* | 12/2016 | Reicher | G06T 7/0014 |

OTHER PUBLICATIONS

Jinyi Qi and Ronald H. Huesman; Theoretical Study of Lesion Detectability of MAP Reconstruction Using Computed Observers; Aug. 2001; pp. 815-822; vol. 20 No. 8; IEEE Transactions on Medical Imaging.

Anastasia Yendiki and Jeffrey A. Fessler; Analysis of Observer Performance in Known-Location Tasks for Tomographic Image Reconstruction; Jan. 2006; pp. 28-41; vol. 25 No. 1; IEEE Transactions on Medical Imaging.

Adam M. Alessio and Paul E. Kinahan; Improved quantitation for PET/CT image reconstruction with system modeling and anatomical priors; Nov. 2006; pp. 4095-4103; 2006 Am. Assoc. Phys. Med.

N. C. Ferreira, R. Trebossen and B. Bendriem; Assessment of 3-D PET Quantitation: Influence of Out of the Field of View Radioactive Sources and of Attenuating Media; Jun. 1998; pp. m1670-m1675; IEEE Transactions on Nuclear Science; vol. 45, No. 3.

* cited by examiner

SYSTEMS AND METHODS FOR EMISSION TOMOGRAPHY QUANTITATION

BACKGROUND OF THE INVENTION

The subject matter disclosed herein relates generally to imaging systems and techniques, and more particularly to imaging for both quantitation and visualization.

In certain types of imaging devices, such as positron emission tomography (PET) scanners, arrays of detector elements are used to detect radiation emanating from the patient. In a PET scanner, for example, arrays of scintillator crystals may be used to detect annihilation photons which are generated inside the patient. The annihilation photons are produced when a positron emitted from a radiopharmaceutical injected into the patient collides with an electron causing an annihilation event. The scintillator crystals receive the annihilation photons and generate light photons in response to the annihilation photons, with the light photons emitted to a photosensor configured to convert the light energy from the light photons to electrical energy used to reconstruct an image.

Various algorithms may be used to reconstruct an image using information acquired during an imaging process. Images may be used, for example, for quantitation, and as another example, for display and/or detection. It may be difficult to optimize a single image reconstruction algorithm for multiple objectives including quantitation accuracy, detection, and visual image quality. An image reconstruction algorithm configured for quantitation may not provide desired results for display or detection, and vice versa. For example, a given image may provide accurate quantitation; however, the image may provide visual image quality that suffers from one or more issues, such as an unnatural appearance and/or increased false positives adversely affecting detection.

BRIEF DESCRIPTION OF THE INVENTION

In accordance with various embodiments, a method is provided that includes acquiring scan data for an object to be imaged using an imaging scanner. The method also includes reconstructing a display image, with one or more processors, using the scan data. Further, the method includes determining, with the one or more processors, one or more aspects of a quantitation imaging algorithm for generating a quantitation image, wherein the one or more aspects of the quantitation imaging algorithm are selected to optimize a quantitation figure of merit for lesion quantitation. The method also includes reconstructing a quantitation image, with the one or more processors, using the scan data and the quantitation imaging algorithm; displaying, on a display device, the display image; determining a region of interest in the display image; determining, for the region of interest, a lesion quantitation value using a corresponding region of interest of the quantitation image; and displaying, on the display device, the lesion quantitation value.

In accordance with various embodiments, a tangible and non-transitory computer readable medium is provided that includes one or more software modules. The one or more software modules are configured to direct one or more processors to acquire scan data for an object to be imaged using an imaging scanner; reconstruct a display image, with one or more processors, using the scan data; determine one or more aspects of a quantitation imaging algorithm for generating a quantitation image, wherein the one or more aspects of the quantitation imaging algorithm are selected to optimize a quantitation figure of merit for lesion quantitation; reconstruct a quantitation image, with the one or more processors, using the emission scan data and the quantitation imaging algorithm; display, on a display device, the display image; determine a region of interest in the display image; determine, for the region of interest, a lesion quantitation value using a corresponding region of interest of the quantitation image; and display, on the display device, the lesion quantitation value.

In accordance with various embodiments, medical imaging detection system is provided that includes a detector unit, a display device, and at least one processor. The detector unit is configured to generate scan data. The display device is operably coupled to the detector unit. The at least one processor is operably coupled to the detector unit and the display device and configured to receive the scan data from the detector unit. The at least one processor is configured to determine one or more aspects of a quantitation imaging algorithm for generating a quantitation image, wherein the one or more aspects of the quantitation imaging algorithm are selected to optimize a quantitation figure of merit for lesion quantitation; reconstruct a display image, with the one or more processors, using the emission scan data; reconstruct a quantitation image, with the one or more processors, using the emission scan data and the quantitation imaging algorithm; display, using the display device, the display image; determine a region of interest in the display image; determine, for the region of interest, a lesion quantitation value using a corresponding region of interest of the quantitation image; and display, on the display device, the lesion quantitation value.

DETAILED DESCRIPTION OF THE INVENTION

Figure 1:
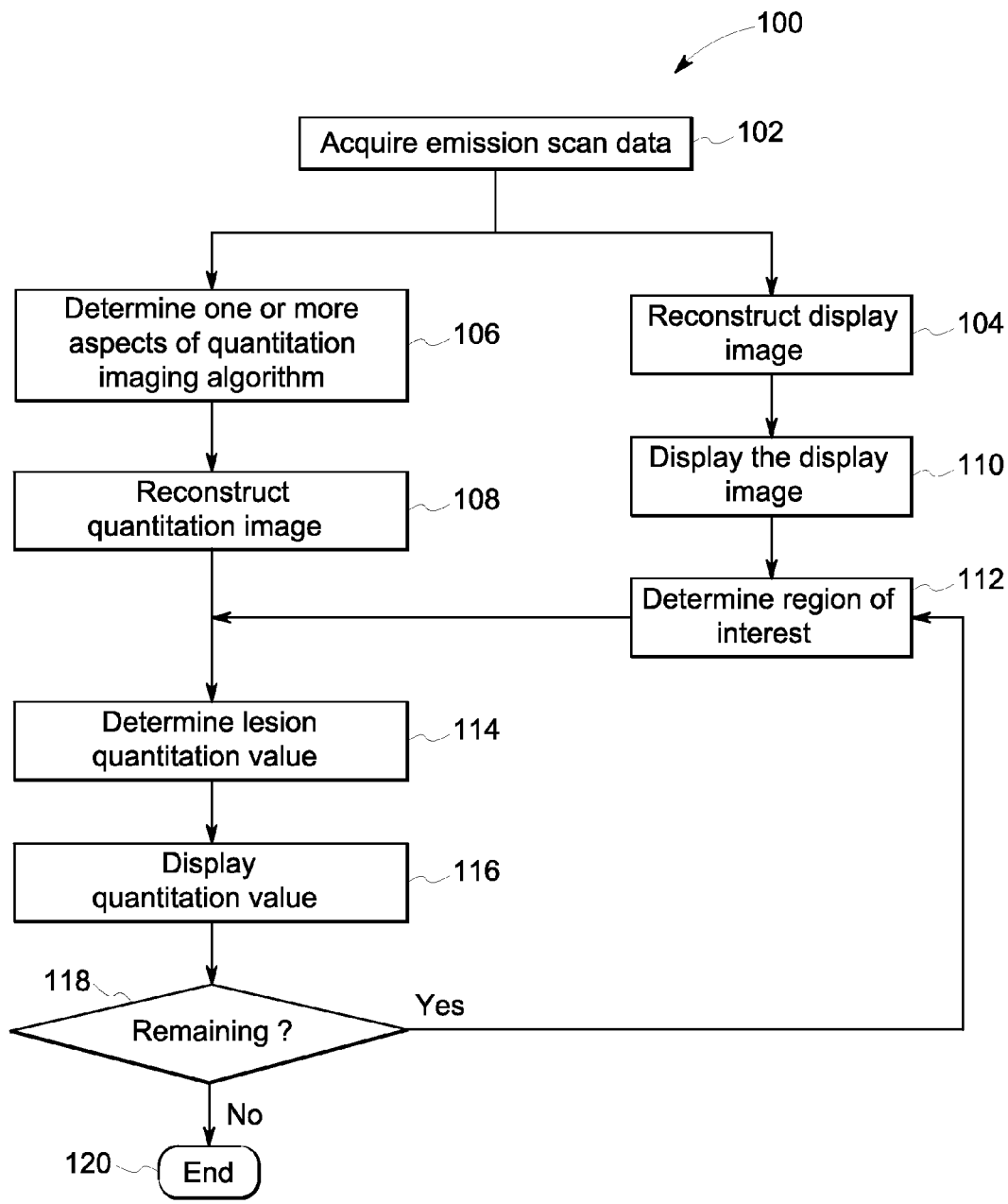
FIG. 1 is a flowchart of a method in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," and "module" include a hardware and/or software system that operates to perform one or more functions. For example, a system, unit, or module may include electronic circuitry that includes and/or is coupled to one or more computer processors, controllers, or other logic based devices that perform operations based on instructions stored on a tangible and non-transitory computer readable storage medium, such as a computer memory. Alternatively or additionally, a system, unit, or module may include a hard-wired device that performs operations based on hard-wired logic of the device. The systems, units, or modules shown in the attached figures may represent the hardware that operates based on software or hardwired instructions, the software that directs hardware to perform the operations, or a combination thereof. "Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described herein. Additionally or alternatively, one or more of these devices may be hard-wired with logic circuits to perform these operations. Further, "systems," "units," or "modules" may be configured to execute one or more algorithms to perform functions or operations described herein. The one or more algorithms may include aspects of embodiments disclosed herein, whether or not expressly identified in a flowchart or as a step of a method.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide methods and systems for generating a visual display image for diagnostic use, as well as for generating a quantitation value (e.g., a lesion quantitation value for a region of interest of the visual display image). For example, a medical imaging system may acquire data for a subject (e.g., patient or object), reconstruct an image from the data, and display the image to a user (e.g., a practitioner or clinician). The user may then specify a region of interest in the displayed image and quantify the image in the region of interest to obtain quantitative information that assists in one or more of diagnosis, staging, or monitoring response to treatment. For example, positron emission tomography (PET) provides an activity or emission image, which corresponds to the distribution of a radiotracer inside a patient. The activity image may be used to detect lesions by a clinician. Further, a clinician may also quantify a region of interest to obtain quantitative information, such as standardized uptake value. In various embodiments, at least two images (e.g., a display image and a quantitation image) are separately and independently reconstructed from data such that one of the images is reconstructed by an algorithm optimized for quantitation and another image is reconstructed by another algorithm optimized for display and/or detection. A system may then display the image optimized for display and/or detection. When a user specifies a region of interest for quantitation in the image optimized for display, the system may then use the image optimized for quantitation to calculate a quantitation value corresponding to the region of interest, and display the quantitation value for the user.

A technical effect of at least some embodiments provides improved diagnostic capability. For example, a technical effect of at least some embodiments includes improved quantitation as well as improved image quality for a visual or display image.

FIG. 1 provides a flowchart of a method 100 (e.g., for visual and quantitation imaging) in accordance with various embodiments. The method, for example, may be configured for use with a PET imaging system. In various embodiments, the method may additionally or alternatively be used with other emission tomography imaging systems, such as a SPECT system. It may be noted that, while certain examples are discussed herein in connection with emission tomography imaging systems, in various other embodiments other types of imaging systems may be employed, including transmission tomography such as x-ray and/or computed tomography (CT). The method 100, for example, may employ, include, or relate to structures or aspects of various embodiments discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be used as one or more algorithms (e.g., software modules or other instructions stored on a tangible and non-transitory computer readable medium utilizing or based on the one or more algorithms) to direct hardware (e.g., processing unit 330 or portion thereof) to perform one or more operations described herein. Generally, as part of the method 100, both a quantitation image (e.g., a representation of acquired emission data for use in quantitation) and a display image (e.g., a representation of acquired emission data for visual display to an operator) are generated.

At 102, emission scan data is acquired. For example, the emission scan data may be acquired using an emission tomography scanner, such as a PET scanning system or a SPECT scanning system, among others. Examples of emission tomography scanners or scanning systems are discussed herein, for example, in connection with FIGS. 3-6.

At 104, a display image is reconstructed using the emission scan data acquired at 102. In some embodiments, the display image may be reconstructed using conventional image reconstruction techniques. It may be noted that the display image is a diagnostic image, or an image having sufficient resolution to allow a practitioner to perform a diagnosis (e.g., lesion identification) using the display image. For the purposes of clarity and avoidance of doubt, lower resolution images such as a scout scan or pre-scan are not display images as used herein. In some embodiments, for example as discussed in connection with FIG. 2 herein, a penalized-likelihood algorithm using predetermined penalty function type, penalty strength and/or penalty parameter values optimized for lesion detection and/or image quality may be employed. It may be noted that, in some embodiments, the display image and a quantitation image, both reconstructed using the emission scan data from 102, may be separately and independently reconstructed.

At 106, one or more aspects of a quantitation imaging algorithm (an algorithm particularly configured, tailored or adapted for a quantitation image) for generating a quantitation image are determined. For example, the form or type of quantitation imaging algorithm may be selected from a group of quantitation imaging algorithms or otherwise determined. Additionally or alternatively, the value of one or more parameters may be selected or determined. In various embodiments, the quantitation imaging algorithm is a penalized-likelihood image reconstruction algorithm configured to be used in conjunction with emission tomography scanning (e.g., PET scanning). The one or more aspects to be determined may include at least one of a penalty function type, a penalty strength or a penalty parameter value for the penalized-likelihood image reconstruction algorithm. The one or more aspects (e.g., at least one of a penalty function type, a penalty strength or a penalty parameter value) may be selected to optimize a quantitation figure of merit for lesion quantitation. The figure of merit, for example, may include one or more of a mean square error, a bias, a signal-to-noise ratio, a contrast recovery coefficient, or a recovery coefficient. It may be noted that the term "optimize" (and forms thereof) are not necessarily intended to require maximizing or minimizing a characteristic, parameter, or other object in all embodiments described herein (in some embodiments, a characteristic, parameter or other object may be maximized). In some embodiments, a characteristic, parameter, or other object may be maximized within one or more given constraints.

The one or more aspects (e.g., at least one of a penalty function type, a penalty strength or a penalty parameter value) may be determined based on at least one of a scanner geometry, a data acquisition protocol, a location of a lesion feature to be quantified in an object (e.g., a location with respect to one or more aspects or portions of an emission tomography scanner), an aggregated certainty value, a size of the lesion feature to be quantified, or a scan duration. Object (or patient) size, scan duration, and scan protocol may all be considered when determining the one or more aspects of the quantitation imaging algorithm in various embodiments. Additionally or alternatively, the one or more aspects may be determined based on one or more of a background activity, or a contrast of the lesion feature.

The particular values for the one or more aspects (e.g., at least one of a penalty function type, a penalty strength or a penalty parameter value) of the quantitation imaging algorithm may be determined based on previous studies using test data, simulated data, clinical data, hybrid clinical data, and/or phantom data. For example, for a particular combination of at least one of scanner geometry, data acquisition protocol, object (or patient) size, scan duration, location of lesion feature to be quantified in the object, and size of the lesion feature, various penalty function types, penalty strengths and/or penalty parameter values may be utilized for reconstructing quantitation images, and the resulting quantitation images may be used for calculating quantitation figures of merit. The particular type of penalty function and/or the particular value(s) of penalty strength and/or penalty parameter that optimize the quantitation figure of merit may be identified for the particular combination of at least one of scanner geometry, data acquisition protocol, location and/or size of lesion feature, scan duration, and aggregate certainty value, where the aggregate certainty value may be calculated as in J. A. Fessler and W. L. Rogers, "Spatial resolution properties of penalized-likelihood image reconstruction methods: space-invariant tomographs," IEEE Transactions on Image Processing, vol. 5, pp. 1346-1358, 1996, and later selected for use for the quantitation imaging algorithm when the same or similar combination of at least one of scanner geometry, data acquisition protocol, location and/or size of lesion feature, scan duration, and aggregate certainty value are utilized in practice. Similarly, the particular type of penalty function and/or the particular value(s) of penalty strength and/or penalty parameter may be identified for other combinations of at least one of scanner geometry, data acquisition protocol, location and/or size of lesion feature, scan duration, and aggregate certainty value. In other words, the particular type of penalty function and/or the particular value(s) of penalty strength and/or penalty parameter may be determined using a look-up table based on previous studies or performing interpolation based on the look-up table. In an alternative embodiment, the particular values for the one or more aspects may be determined based on calculating and/or approximating a Fisher information matrix and using approximate analytical expressions for local impulse responses and/or a covariance matrix. The local impulses and/or the covariance matrix may be calculated as in J. A. Fessler and W. L. Rogers, "Spatial resolution properties of penalized-likelihood image reconstruction methods: space-invariant tomographs," IEEE Transactions on Image Processing, vol. 5, pp. 1346-1358, 1996 and J. A. Fessler, "Mean and variance of implicitly defined biased estimators (such as penalized maximum likelihood): applications to tomography," IEEE Transactions on Image Processing, vol. 5, pp. 493-506, 1996.

In another embodiment, for a given acquired scan dataset, the particular values for the one or more aspects (e.g., at least one of a penalty function type, a penalty strength or a penalty parameter value) of the quantitation imaging algorithm may be determined based on analyzing quantitation images with and without the presence of a lesion. An exemplary method to reconstruct the quantitation images with and without a lesion is to generate a derived synthetic scan dataset by digitally inserting a lesion of known size and activity concentration into the acquired scan dataset, and then to reconstruct quantitation images from the derived synthetic scan dataset and the original acquired scan dataset, respectively. Various penalty function types, penalty strengths and/or penalty parameter values may be utilized to optimize the quantitation figure of merit that measures quantitative accuracy such as contrast recovery coefficient, recovery coefficient, and bias in reconstructed activity, which may be calculated by comparison with the known activity concentration of the digitally inserted lesion. This approach may be called hybrid lesion insertion.

Certain aspects of penalized-likelihood image reconstruction will now be discussed. It may be noted that, in emission tomography (e.g., PET or SPECT), ordered subsets expectation maximization (OSEM) algorithms may be used for image reconstruction. Algorithm parameters for OSEM include iteration number and post-reconstruction filter parameters. A user or algorithm designer may tune iteration number and/or post-reconstruction filter parameters in order to control the image quality or the trade-off between image resolution and image noise. It may be noted that more accurate models for physics and statistical noise may be used with OSEM than with an analytical image reconstruction method such as filtered backprojection (FBP). OSEM techniques, however, may not provide a desired level of predictability and/or quality.

An alternative class of image reconstruction algorithms is penalized-likelihood image reconstruction, which may also be referred to as regularized reconstruction and maximum a posteriori (MAP) reconstruction. In penalized-likelihood reconstruction, the image quality and the resolution-noise trade-off are controlled through a penalty function, also known as a regularization function, and its parameter(s). Since penalized-likelihood image reconstruction algorithms are run until practical convergence, the iteration number is not an algorithm parameter for penalized-likelihood reconstruction, in contrast to OSEM. The type and the parameter(s) of a penalty function used in penalized-likelihood image reconstruction determine the image quality and the resolution-noise trade-off in reconstructed images. One of the advantages of penalized-likelihood reconstruction is that the properties of reconstructed images such as resolution and noise are often predictable and the penalty parameters can be determined or optimized in order to obtain desired image properties or to maximize figures-of-merit relevant to clinical tasks including detection and quantitation.

In various embodiments, penalized-likelihood image reconstruction may be performed by maximizing the penalized-likelihood objective function:

$$\phi(\lambda) = L(\lambda) - R(\lambda)$$

where $\lambda$ denotes the unknown emission activity image, $L(\lambda)$ is the likelihood function, and $R(\lambda)$ is the regularization (or penalty) function. The likelihood function, based on Poisson statistical models, is given by $$L(\lambda) = \sum_i y_i \log([P\lambda]_i + r_i) - ([P\lambda]_i + r_i)$$

where $y_i$ are measured emission scan data for PET, time-of-flight PET or SPECT, P is the forward projector or the system model, and $r_i$ are background contributions including scatters and random coincidences, which are estimated prior to image reconstruction.

In some embodiments, a regularization function may have the following form:

$$R(\lambda) = \beta \sum_{j,k} w_{jk} \psi(\lambda_j, \lambda_k; \theta)$$

where $\beta$ is the global regularization (or penalty) parameter, which determines the global strength of the regularization, $w_{jk}$ are weights applied to voxels j and k, $\psi$ is a potential function or a penalty function, and $\theta$ denotes optional parameters of the penalty function $\psi$. Typically, the weights $w_{jk}$ are zero when voxels j and k are not neighbors; and the weights can vary with the distance between voxels j and k, (e.g., the weights are inversely proportional to the distance). The weights may have a factored form $w_{jk} = \beta_{jk} w_{jk}^0$ where $w_{jk}^0$ varies with the distance between voxels j and k and are non-zero only when voxels j and k are neighbors, and $\beta_{jk}$ are factors that spatially modulate the regularization strength. Therefore, $\theta$ denotes penalty parameter(s), and $\beta$ and/or $\beta_{jk}$ denote penalty strength values.

Different types of penalty function $\psi$ may be employed in various embodiments. For example, a quadratic or Gaussian penalty function used in some embodiments may have the following form:

$$\psi(\lambda_j, \lambda_k) = \frac{1}{2}(\lambda_j - \lambda_k)^2$$

where there is no penalty parameter $\theta$. The generalized Gaussian penalty has the form of:

$$\psi(\lambda_j, \lambda_k; \theta) = |\lambda_j - \lambda_k|^p$$

for some $1 \leq p \leq 2$ where the penalty parameter is given by $\theta = p$. As p approaches 1 from 2, the generalized Gaussian penalty function approaches $|\lambda_j - \lambda_k|$, with more edge-preservation properties. The Huber penalty may take the following form:

$$\psi(\lambda_j, \lambda_k; \theta) = \begin{cases} \frac{1}{2}(\lambda_j - \lambda_k)^2, & |\lambda_j - \lambda_k| \leq \delta \\ \delta|\lambda_j - \lambda_k| - \frac{1}{2}\delta^2, & |\lambda_j - \lambda_k| > \delta \end{cases}$$

It may be noted that the Huber penalty given above has an edge-preserving property, too, where the penalty parameter $\theta = \delta$ determines the location of transition from quadratic to linear functions. Another type of penalty function is the relative difference penalty, which may take the following form:

$$\psi(\lambda_j, \lambda_k; \theta) = \frac{(\lambda_j - \lambda_k)^2}{\lambda_j + \lambda_k + \gamma|\lambda_j - \lambda_k|}$$

where the penalty parameter $\gamma$ controls the degree of edge preservation. As $\gamma$ increases, the relative difference penalty function approaches $|\lambda_j - \lambda_k|$, which has an edge-preserving property. The relative difference penalty is not only a function of $|\lambda_j - \lambda_k|$ but also depends on the voxel intensities through the term $(\lambda_j + \lambda_k)$. Other types of penalty functions may be employed in various embodiments.

The penalized-likelihood objective function may be maximized or otherwise optimized by an iterative numerical optimization algorithm, resulting in a reconstructed image. Numerical optimizers that converge to an optimal point or have reasonable convergence properties may be used to maximize or otherwise optimize the penalized-likelihood objective function, including block sequential regularized expectation maximization (BSREM), preconditioned conjugate gradient (PCG), gradient methods, incremental gradient methods and Newton's methods.

With continued reference to FIG. 1, at 108, a quantitation image is reconstructed using the emission scan data acquired at 102. The quantitation image is reconstructed using the quantitation imaging algorithm with the one or more aspects determined at 106. In the illustrated embodiments, the quantitation image is reconstructed separately and independently from the display image. In various embodiments, the display image may be particularly tailored for lesion identification, while the quantitation image is particularly tailored for quantitation of a selected region of interest or regions of interest. By using separately reconstructed images for quantitation and display, both the quantitation and display images may be more finely tailored for their respective desired purposes.

At 110, the display image reconstructed at 104 is displayed (e.g., on a display device as discussed in connection with FIG. 4 herein). The display image may be displayed to a practitioner or other operator, with the display image used to identify one or more regions of interest of the display image for which quantitation results are desired.

At 112, a region of interest is determined. For example, the region of interest may be determined based on a received input from an operator viewing the image displayed at 110. In some embodiments, for example, the display image may be displayed on a touchscreen, and an operator using a finger or stylus may circle or otherwise indicate one or more regions of interest corresponding to lesions. In other embodiments, a cursor, keypad, or other input device may be utilized to specify one or more regions of interest for the display image.

At 114, a lesion quantitation value is determined. For example, a region of interest for the quantitation image (or a quantitation region of interest) may be determined based on the selected region of interest for the display image. In some embodiments, because the display image and the quantitation image, even if reconstructed separately, are still reconstructed from the same emission scan data, the display image and the quantitation image may be effectively co-registered. Alternatively or additionally, other techniques (e.g., use of anatomical landmarks) may be used to determine the location of a corresponding quantitation region of interest for a selected or otherwise determined display image region of interest. With the quantitation region of interest determined, a quantitation value may be determined for the display region of interest based on values within the corresponding quantitation image region of interest. For example, a standardized uptake value (SUV) for the quantitation image region of interest may be determined and used as a lesion quantitation value for a lesion defined by a selected display region of interest. As used herein, a standardized uptake value may be understood as an uptake value for an emission scan that has been normalized by patient size (e.g., weight) and dose (e.g., dosage of administered imaging radiopharmaceutical). The determined quantitation value, for example, may be a maximum SUV for the quantitation image region of interest. As another example, the determined quantitation value may be a mean SUV, a peak SUV, or other statistical measure of the SUV for the quantitation image region of interest. It may be noted that an SUV and/or other quantitation value may be useful for monitoring the progress of a treatment. For example, if the quantitation value for a given lesion does not change during the course of a treatment, the treatment may be understood as not producing desired results. However, if the quantitation value for a given lesion corresponds to improved health, the treatment may be understood as providing positive results.

At 116, the quantitation value is displayed. For example, the quantitation value may be displayed on the same display device used at 110 to display the display image. The quantitation value may be displayed concurrently with the display image. Further, the quantitation value may be associated with the region of interest for which the quantitation value has been determined. For example, the quantitation value may be displayed near the region of interest. As another example, the quantitation value may be joined by a leader displayed on a screen to the region of interest. As another example, the quantitation value may be associated with the region of interest via a common labelling and/or coloring scheme (e.g., a quantitation value for a first region of interest and the first region of interest both labelled with a "1" or an "a"; a quantitation value for a second region of interest and the second region of interest both labelled with a "2" or a "b," and so on). Alternatively or additionally, the quantitation value (and/or display image) may be displayed on a remote display device, stored for later viewing, and/or printed out.

At 118, it is determined if there are any remaining regions of interest to be quantitatively analyzed. If there are any more remaining regions of interest or lesions to be analyzed, the method 100 returns to 112 for determination of a subsequent region of interest for quantitation analysis. If there are no more remaining regions of interest, the method 100 may end at 120.

Figure 2:
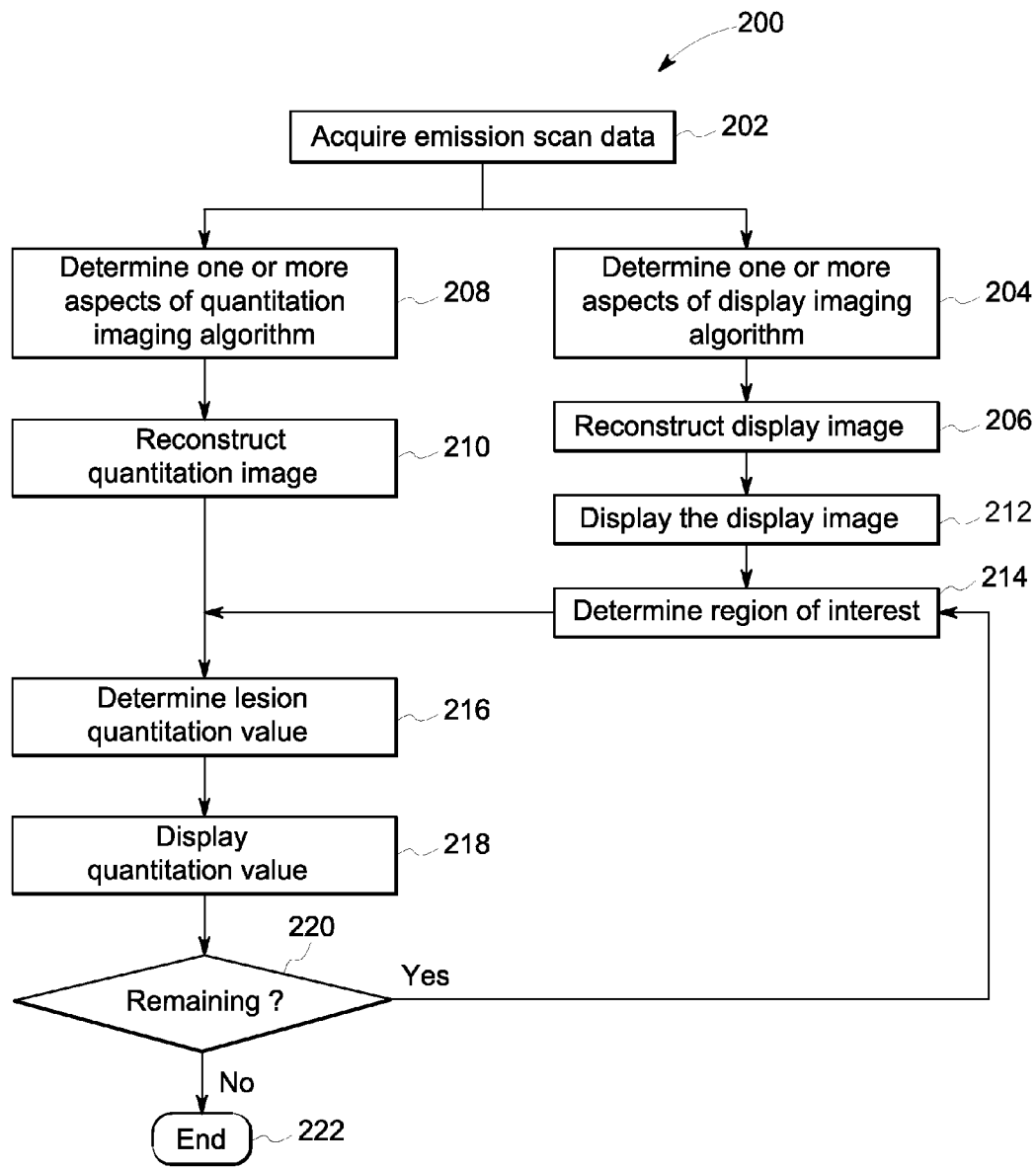
FIG. 2 is a flowchart of a method in accordance with various embodiments.

FIG. 2 provides a flowchart of a method 200 (e.g., for visual and quantitation imaging) in accordance with various embodiments. The method, for example, may be configured for use with a PET imaging system. In various embodiments, the method may additionally or alternatively be used with other emission tomography imaging systems, such as a SPECT system. The method 200, for example, may employ, include, or relate to structures or aspects of various embodiments discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms (e.g., software modules or other instructions stored on a tangible and non-transitory computer readable medium utilizing or based on the one or more algorithms) to direct hardware (e.g., processing unit 330 or portion thereof) to perform one or more operations described herein. Generally, as part of the method 200, both a quantitation image (e.g., a representation of acquired emission data for use in quantitation) and a display image (e.g., a representation of acquired emission data for visual display to an operator) are generated. It may be noted that, in various embodiments, certain of the depicted steps of the method 200 may be generally similar to corresponding steps of the method 100 discussed herein (e.g., 202 may be generally similar to 102, 208 may be generally similar 106, and so on).

At 202, emission scan data is acquired. For example, the emission scan data may be acquired using an emission tomography scanner, such as a PET scanning system or a SPECT scanning system, among others. Examples of emission tomography scanners or scanning systems are discussed herein, for example, in connection with FIGS. 3-6.

At 204, one or more aspects of a display imaging algorithm (an algorithm particularly configured, tailored or adapted for a display image, or an image to be visually presented to a practitioner for diagnostic purposes, such as lesion identification or detection) for generating a display image are determined. For example, the form or type of display imaging algorithm may be selected from a group of display imaging algorithms or otherwise determined. Additionally or alternatively, the value of one or more parameters may be selected or determined. In various embodiments, the display imaging algorithm is a penalized-likelihood image reconstruction algorithm configured to be used in conjunction with emission tomography scanning (e.g., PET scanning). The one or more aspects to be determined may include at least one of a penalty function type, a penalty strength or a penalty parameter value for the penalized-likelihood image reconstruction algorithm. The one or more aspects (e.g., at least one of a penalty function type, a penalty strength or a penalty parameter value) may be selected to optimize a display figure of merit for lesion identification (or detection) and/or visual image quality. Alternatively or additionally, the one or more aspects (e.g., at least one of a penalty function type, a penalty strength or a penalty parameter value) may be selected to optimize a display figure of merit for visual image quality. The figure of merit for lesion identification (or detection), for example, may include one or more of a signal-to-noise ratio, a lesion detectability index, or an area under a receiver operating characteristic curve. The figure of merit for visual image quality, for example, may include a subjective image quality score. Such an image quality score may be developed, for example, by measuring the perceived image quality (including lesion conspicuity, image noise, and image artifacts) of various test images viewed by a group of observers. It may be noted that, in some embodiments, the display imaging algorithm may be a penalized-likelihood image reconstruction algorithm having a substantially similar form as the quantitation imaging algorithm discussed in connection with 106 and 208, but may utilize different penalty function type, penalty strength, penalty parameter value(s), or other aspects or parameters.

The one or more aspects of the display imaging algorithm (e.g., at least one of a penalty function type, a penalty strength or a penalty parameter value) may be determined based on at least one of a scanner geometry, a data acquisition protocol, a location of a lesion feature (e.g., a location with respect to one or more aspects or portions of an emission tomography scanner), an aggregated certainty value, a size of the lesion feature, or a scan duration. Object (patient) size, scan duration, and scan protocol may all be considered when determining the one or more aspects of the display imaging algorithm in various embodiments. Additionally or alternatively, the one or more aspects may be determined based on one or more of a background activity, or a contrast of the lesion feature.

As with the particular values for the one or more aspects of a quantitation imaging algorithm, the particular values for the one or more aspects (e.g., at least one of a penalty function type, a penalty strength or a penalty parameter value) of the display imaging algorithm may be determined based on previous studies using test data, simulated data, clinical data, hybrid clinical data, and/or phantom data. For example, for a particular combination of scanner geometry, data acquisition protocol, object (or patient) size, scan duration, location of lesion feature, and size of the lesion feature, various penalty function types, penalty strengths and/or penalty parameter values may be utilized for reconstructing display images, and the resulting display images may be used for calculating imaging figures of merit (for lesion detection or visual image quality). The particular type of penalty function and/or the particular value(s) of penalty strength and/or penalty parameter that optimize the imaging figure of merit may be identified for the particular combination of at least one of scanner geometry, data acquisition protocol, location and/or size of lesion feature, scan duration, and aggregate certainty value, and later selected for use for the display imaging algorithm when the same or similar combination of at least one of scanner geometry, data acquisition protocol, location and/or size of lesion feature, scan duration, and aggregate certainty value are utilized in practice. Similarly, the particular type of penalty function and/or the particular value(s) of penalty strength and/or penalty parameter may be identified for other combinations of at least one of scanner geometry, data acquisition protocol, location and/or size of lesion feature, scan duration, and aggregate certainty value. In other words, the particular type of penalty function and/or the particular value(s) of penalty strength and/or penalty parameter may be determined using a look-up table based on previous studies or performing interpolation based on the look-up table. In an alternative embodiment, the particular values for the one or more aspects may be determined based on calculating and/or approximating a Fisher information matrix and using approximate analytical expressions for local impulse responses and/or a covariance matrix. Previously, such techniques have been proposed to optimize the penalty strength for lesion detectability based on closed-form theoretical expressions. (See, e.g., J. Qi and R. H. Huesman, "Theoretical study of lesion detectability of MAP reconstruction using computer observers," IEEE Transactions on Medical Imaging, vol. 20, pp. 815-822, 2001; see also A. Yendiki and J. A. Fessler, "Analysis of observer performance in known-location tasks for tomographic image reconstruction," IEEE Transactions on Medical Imaging, vol. 25, pp. 28-41, 2006.) These expressions are mostly accurate for quadratic penalty functions and are less accurate for non-quadratic penalty functions and therefore are not extensible to optimizing the penalty function type In another embodiment, for a given acquired scan dataset, the particular values for one or more aspects (e.g., at least one of a penalty function type, a penalty strength or a penalty parameter value) of the display imaging algorithm may be determined based on a lesion detectability index from a computer observer model. The inputs for the computer observer model are two image volumes, one with a lesion present and another without a lesion present. An exemplary method to reconstruct the two image volumes with and without a lesion is to generate a derived synthetic scan dataset by digitally inserting a lesion of known size and activity concentration into the acquired scan dataset, and then to reconstruct images from the derived synthetic scan dataset and the original acquired scan dataset, respectively. Various penalty function types, penalty strengths and/or penalty parameter values may be utilized to optimize the lesion detection index. This approach may be called hybrid lesion insertion.

At 206, a display image is reconstructed using the emission scan data acquired at 202, and using the display imaging algorithm for which one or more aspects were determined at 204. It may be noted that, as also discussed in connection with 110 of FIG. 1, the display image is a diagnostic image, or an image having sufficient resolution to allow a practitioner to perform a diagnosis (e.g., lesion identification or detection) using the display image.

At 208, one or more aspects of a quantitation imaging algorithm (an algorithm particularly configured, tailored or adapted for a quantitation image) for generating a quantitation image are determined. The determination at 208 in various embodiments may be generally similar to the determination at 106 of the method 100 discussed herein. For example, the form or type of quantitation imaging algorithm may be selected from a group of quantitation imaging algorithms or otherwise determined. Additionally or alternatively, the value of one or more parameters may be selected or determined. The one or more aspects to be determined may include at least one of a penalty function type, a penalty strength or a penalty parameter value for the penalized-likelihood image reconstruction algorithm. The one or more aspects (e.g., at least one of a penalty function type, a penalty strength or a penalty parameter value) may be selected to optimize a quantitation figure of merit for lesion quantitation. The figure of merit, for example, may include one or more of a mean square error, a bias, a signal-to-noise ratio, a contrast recovery coefficient, or a recovery coefficient.

At 210, a quantitation image is reconstructed using the emission scan data acquired at 202. In the depicted embodiment, the quantitation image is reconstructed using the quantitation imaging algorithm with the one or more aspects determined at 208. In the illustrated embodiments, the quantitation image is reconstructed separately and independently from the display image.

At 212, the display image reconstructed at 206 is displayed (e.g., on a display device as discussed in connection with FIG. 4 herein). The display image may be displayed to a practitioner or other operator, with the display image used to identify one or more regions of interest of the display image for which quantitation results are desired.

At 214, a region of interest is determined. For example, the region of interest may be determined based on a received input from an operator viewing the image displayed at 212. In some embodiments, for example, the display image may be displayed on a touchscreen, and an operator using a finger or stylus may circle or otherwise indicate one or more regions of interest corresponding to lesions. In other embodiments, a cursor, keypad, or other input device may be utilized to specify one or more regions of interest for the display image.

At 216, a lesion quantitation value is determined. For example, a region of interest for the quantitation image (or a quantitation region of interest) may be determined based on the selected region of interest for the display image. With the quantitation region of interest determined, a quantitation value may be determined for the display region of interest based on values within the corresponding quantitation image region of interest. For example, a standardized uptake value (SUV) for the quantitation image region of interest may be determined and used as a lesion quantitation value for a lesion defined by a selected display region of interest.

At 218, the quantitation value is displayed. For example, the quantitation value may be displayed on the same display device used at 212 to display the display image. The quantitation value may be displayed concurrently with the display image. Further, the quantitation value may be associated with the region of interest for which the quantitation value has been determined. Alternatively or additionally, the quantitation value (and/or display image) may be displayed on a remote display device, stored for later viewing, and/or printed out.

At 220, it is determined if there are any remaining regions of interest to be quantitatively analyzed. If there are any more remaining regions of interest or lesions to be analyzed, the method 200 returns to 214 for determination of a subsequent region of interest for quantitation analysis. If there are no more remaining regions of interest, the method 200 may end at 222.

Figure 3:
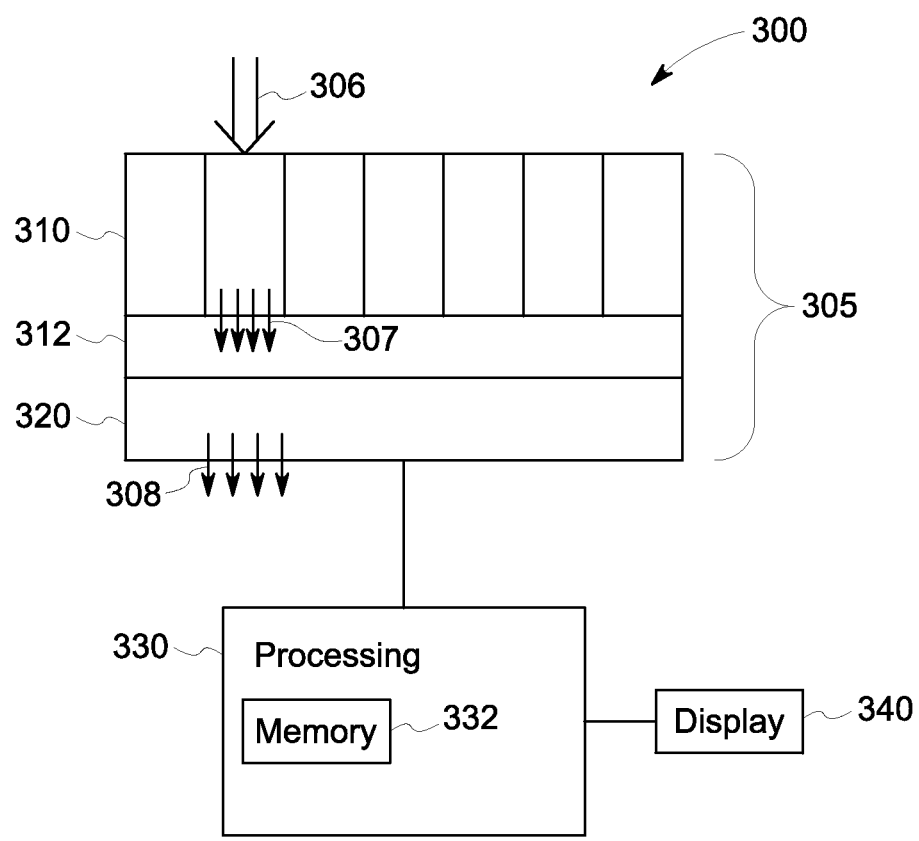
FIG. 3 is a schematic diagram of a PET detection system in accordance with various embodiments.

FIG. 3 provides a schematic diagram of a radiation detection system 300 (e.g., PET detection system 300) formed in accordance with various embodiments, which may be utilized in connection with methods or processes discussed herein or aspects thereof (e.g., in connection with one or more aspects of the method 100 and/or the method 200 discussed herein). The depicted PET detection system 300 includes a detector unit 305 and a processing unit 330, as well as a display 340. It may be noted that one or more aspects of the detector unit 305 and the processing unit 330 may be integrally formed or otherwise disposed in a common housing. Generally, the PET detection system 300 is configured to receive a photon or gamma ray, and provide an output indicative of the energy of the gamma ray, the location of impact of the gamma ray, and the timing of the impact of the gamma ray to the processing unit 330. The reconstruction processing unit may then use the information from the PET detection system 300 and other generally similar PET detection systems disposed about an object to be imaged to reconstruct an image of at least a portion of the object to be imaged. It may further be noted that the PET detection system is one example of a radiation or emission detection system, and the other types of detection systems may be utilized in various embodiments.

The depicted detector unit 305 includes a crystal array 310, a light guide 312, and a photosensor unit 320. Generally, an annihilation photon 306 impacts the crystal array 310, and the crystal array 310 generates light photons 307 responsive to the annihilation photon 306. The light photons 307 impact the photosensor unit 320, which provides signals 308 (e.g., to the processing unit 330) corresponding to the reception of the light photons 307. Signals 308 corresponding to annihilation photon or gamma ray impact on the various crystals may be used to determine the energy and location of impacts, which may be used to reconstruct the image. It may be noted that each photon impact may also be referred to as a radiation event. For example, a given annihilation photon impact may be a singles event. Two opposed singles events on a common line of response within a predetermined time range of each other may be determined to correspond to a coincidence event, with the coincidence events used to reconstruct an image.

The depicted crystal array 310 is configured to be impacted by gamma rays or photons during a PET scan and to produce light in response to being impacted by gamma rays or photons. The crystal array 310 is an example of a scintillator block that produces light in response to the impact of gamma rays or photons. The light may be detected by an associated photosensor (e.g. Silicon photomultiplier (SiPM)) and used to reconstruct an image. The crystal array 310 may be formed, for example, from a group of crystals, with one or more internal light barriers between groups of crystals. For ease of illustration and clarity of description, it may be noted that only one crystal array 310 and only one PET detection system 300 are shown in FIG. 3. It may be noted that, in practice, multiple generally similar PET detection systems 300 may be disposed about an object being imaged (e.g., in a ring), with photons from a given annihilation event striking opposite crystal arrays or detection systems 300. The particular numbers and/or arrangement of detections systems, crystals, and photosensors (and/or photosensor regions) for the various embodiments depicted and/or discussed herein are provided by way of example. Other numbers and/or arrangements may be employed in various embodiments.

In the embodiment depicted in FIG. 3, the processing unit 330 is operably coupled to the detector unit 305. The depicted processing unit 330 is configured (e.g., may include one or more ASIC's and/or FPGA's, and/or includes or is associated with a tangible and non-transitory memory having stored thereon instructions configured to direct the processor) to, for example, determine one or more aspects of a quantitation imaging algorithm (and/or display imaging algorithm) as discussed herein in connection with FIGS. 1 and 2, acquire emission scan data for an object to be imaged, reconstruct a display image using the acquired emission scan data, reconstruct a quantitation image using the acquired emission scan data, display (e.g., using the display device 340) the display image, determine a region of interest in the display image, determine, for the region of interest, a lesion quantitation value using a corresponding region of interest of the quantitation image, and display the lesion quantitation value.

In various embodiments the processing unit 330 includes processing circuitry configured to perform one or more tasks, functions, or steps discussed herein. It may be noted that "processing unit" as used herein is not intended to necessarily be limited to a single processor or computer. For example, the processing unit 330 may include multiple processors, ASIC's, FPGA's, and/or computers, which may be integrated in a common housing or unit, or which may be distributed among various units or housings. It may be noted that operations performed by the processing unit 330 (e.g., operations corresponding to process flows or methods discussed herein, or aspects thereof) may be sufficiently complex that the operations may not be performed by a human being within a reasonable time period. For example, the determination of aspects of imaging algorithms, the processing of imaging algorithms to reconstruct images, and/or the determination of quantitation values for regions of interest may rely on or utilize computations that may not be completed by a person within a reasonable time period.

As seen in FIG. 3, the processing unit 330 includes a memory 332. The memory 332 may include one or more computer readable storage media (e.g., tangible and non-transitory storage media). The memory 332, for example, may store information corresponding to the energy values of one or more signals, count information for obtained counts, quantitation values for images, results of intermediate processing steps, or the like. For example, the memory 332 may have stored thereon one or more formulae or look-up tables that may be utilized to determine penalty strength and/or penalty value parameters as discussed herein, for example as part of a pre-calculation of a figure of merit. Further, the process flows and/or flowcharts discussed herein (or aspects thereof) may represent one or more sets of instructions that are stored in the memory 332 for direction of operations of the PET detection system 300.

The display device 340, as discussed herein, is operably connected with the processing unit 330, and is configured to display images and/or quantitation results generated by the processing unit 330. The display device 340 may include, for example, a touchscreen or other input device configured to receive input from a practitioner. For example, a practitioner may select a region of interest upon which quantitation is to be performed by outlining the region of interest on a touchscreen or providing another input. Alternately or additionally, the processing unit 340 may receive input information either automatically or from a user specifying scan protocol, scan duration, or other information upon which one or more aspects of a quantitation imaging algorithm and/or visual imaging algorithm are to be based.

Figure 4:
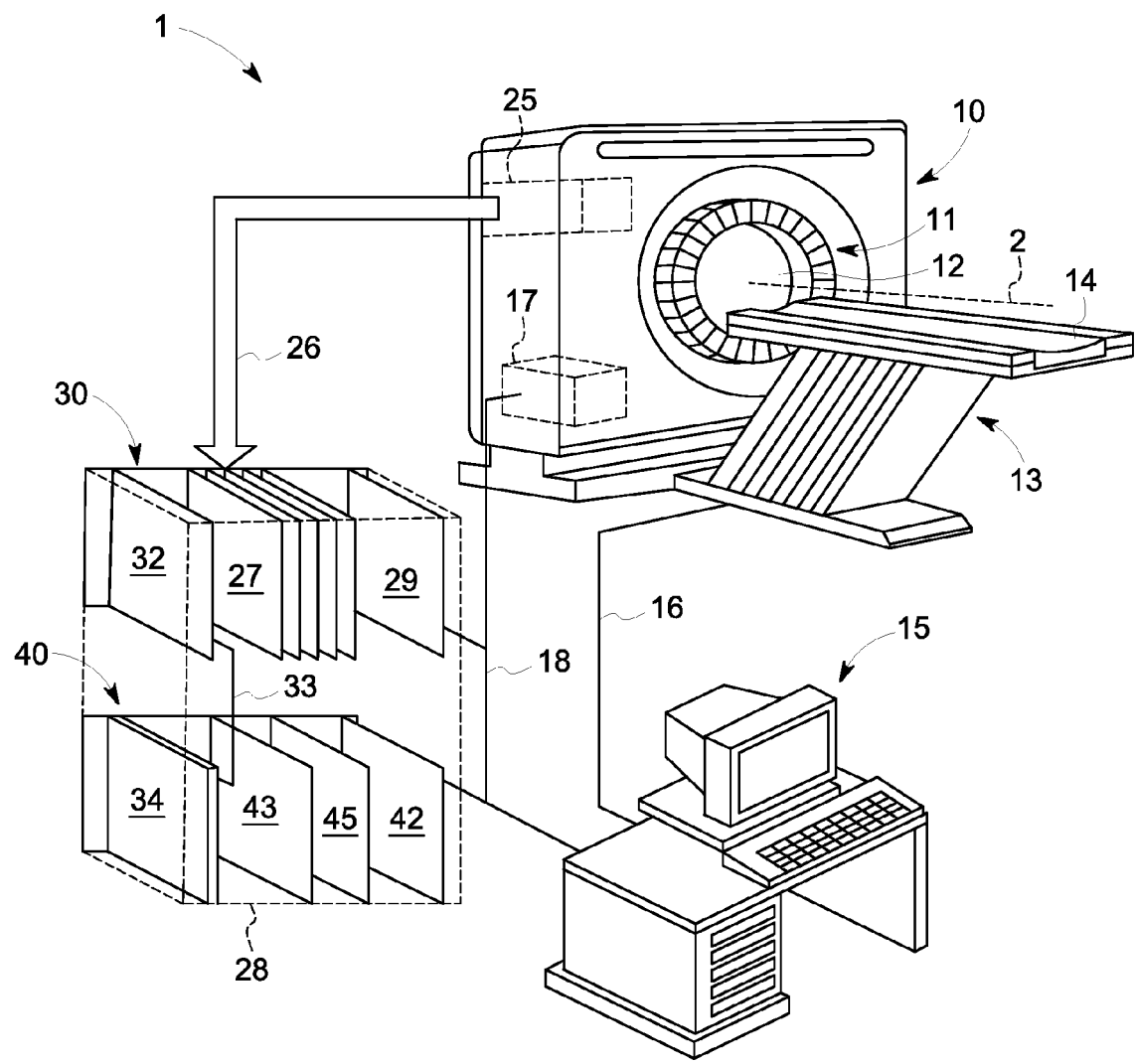
FIG. 4 illustrates an imaging system in accordance with various embodiments.
Figure 5:
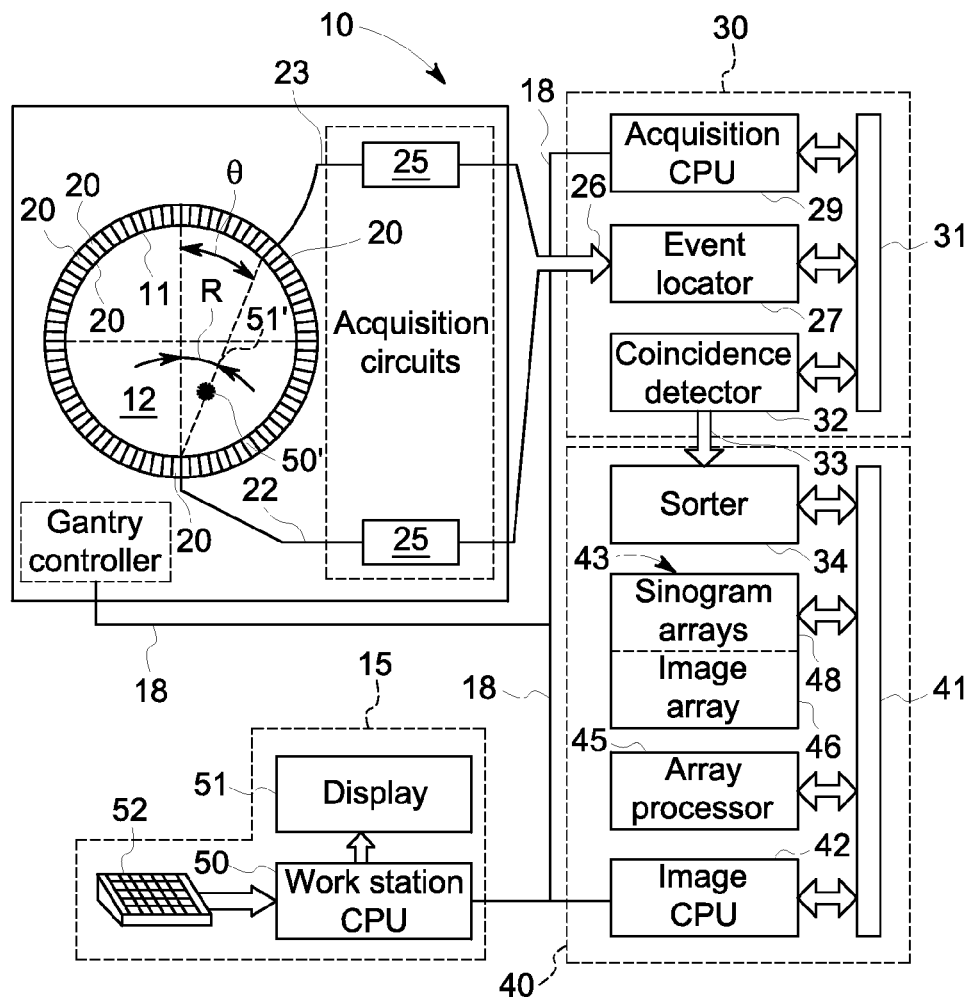
FIG. 5 is a schematic diagram of the imaging system of FIG. 4.
Figure 6:
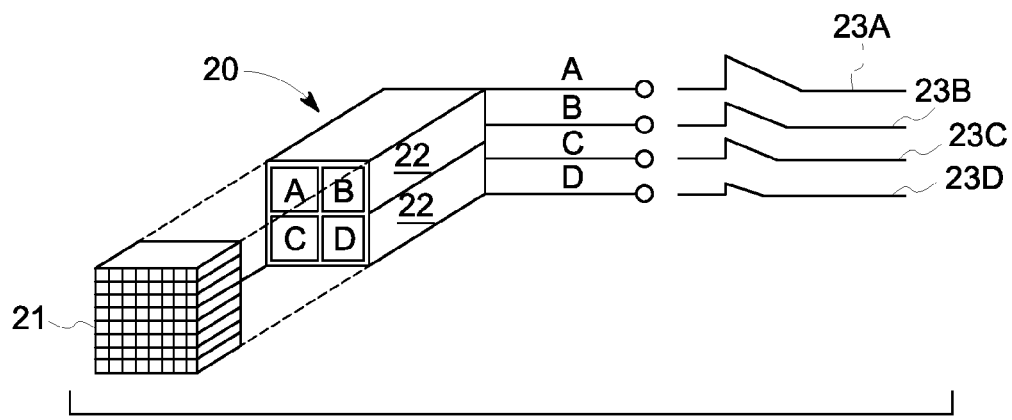
FIG. 6 illustrates an example of a detector module which forms part of the imaging system in accordance with various embodiments.

FIGS. 4-6 illustrate a PET imaging system with which various embodiments described herein may be employed. In other embodiments, crystal arrays as discussed herein may be utilized with other imaging systems (e.g., imaging systems configured for one or more additional or alternative modalities). FIG. 4 illustrates a PET scanning system 1 including a gantry 10 that supports a detector ring assembly 11 about a central opening or bore 12. The detector ring assembly 11 in the illustrated embodiments is generally circular and is made up of plural rings of detectors spaced along a central axis 2 to form a cylindrical detector ring assembly. In various embodiments, the detector ring assembly 11 may include 5 rings of detectors spaced along the central axis 2. A patient table 13 is positioned in front of the gantry 10 and is aligned with the central axis 2 of the detector ring assembly 11. A patient table controller (not shown) moves the table bed 14 into the bore 12 in response to commands received from an operator work station 15 through a communications link 16. A gantry controller 17 is mounted within the gantry 10 and is responsive to commands received from the operator work station 15 through a second communication link 18 to operate the gantry.

As shown in FIG. 5, the operator work station 15 includes a central processing unit (CPU) 50, a display 51, and a keyboard 52. An operator may use the keyboard to control the calibration of the PET scanner, the configuration of the PET scanner, and the positioning of the patient table for a scan. Also, the operator may control the display of the resulting image on the display 51 and/or perform image enhancement functions using programs executed by the work station CPU 50.

The detector ring assembly 11 includes a number of detector modules. For example, the detector ring assembly 11 may include 36 detector modules, with each detector module including eight detector blocks. An example of one detector block 20 is shown in FIG. 6. The detector blocks 20 in a detector module may be arranged, for example, in a 2×4 configuration such that the circumference of the detector ring assembly 11 is 72 blocks around, and the width of the detector assembly 11 is 4 detector blocks wide. Each detector block 20 may include a number of individual detector crystals. In the illustrated embodiment, the array of detector crystals 21 is situated in front of four photosensors 22. The photosensors 22 are depicted schematically as photomultiplier tubes; however, it may be noted that SiPM's may be employed in various embodiments. Other configurations, sized and numbers of detector crystals, photosensors and detector modules may be employed in various embodiments.

During a PET scan, an annihilation photon may impact one of the detector crystals 21. The detector crystal 21, which may be formed, for example of lutetium yttrium silicate (LYSO) or bismuth germinate (BGO), for example, converts the annihilation photon into a number of photons which are received and detected by the photosensors. The photons generated by a detector crystal generally spread out to a certain extent and travel into adjacent detector crystals such that each of the four photosensors 22 receives a certain number photons as a result of an annihilation photon impacting a single detector crystal 21.

In response to a scintillation event, each photosensor 22 produces a signal 23A-23D on one of the lines A-D, as shown in FIG. 6, which rises sharply when a scintillation event occurs and then tails off exponentially. The relative magnitudes of the signals are determined by the position in the detector crystal array at which the scintillation event took place. The energy of the annihilation photon which caused the scintillation event determines the total magnitude of the four signals. The time that the signal begins to rise is determined by when the scintillation event occurs and the time required for photons to travel from the position of the scintillation event to the photosensors. The example depicted in FIG. 6 provides an example based on a vacuum photodetector; however, it may be noted that certain principles disclosed herein may also be applied to SiPM detectors generally.

As shown in FIG. 5, a set of acquisition circuits 25 is mounted within the gantry 10 to receive the four signals from the detector block 20. The acquisition circuits 25 determine timing, energy and the event coordinates within the array of detector crystals using the relative signal strengths. The results are digitized and sent through a cable 26 to an event locator circuit 27 housed in a separate cabinet 28. Each acquisition circuit 25 also produces an event detection pulse which indicates the exact moment the scintillation event took place.

The event locator circuits 27 form part of a data acquisition processor 30 which periodically samples the signals produced by the acquisition circuits 25. The data acquisition processor 30 has an acquisition CPU 29 which controls communications on the local area network 18 and a bus 31. The event locator circuits 27 assemble the information regarding each valid event into a set of digital numbers that indicated when the event took place and the identity of the detector crystal 21 which detected the event. The event locator circuits 27, for example, may use a detector position map to map a pair of coordinates to the detector 21 which detected the event.

The event data packets are transmitted to a coincidence detector 32 which is also part of the data acquisition processor 30. The coincidence detector 32 accepts the event data packets from the event locator circuits 27 and determines if any two of them are in coincidence. Coincidence is determined by a number of factors. For example, time markers in each event data packet may be required to be within a specified time period of each other, e.g., 6 nanoseconds. As another example, the locations indicated by the two event data packets may be required to lie on a straight line which passes through the field of view (FOV) in the scanner bore 12. Events which cannot be paired are discarded, but coincident event pairs are located and recorded as a coincidence data packet that is transmitted through a serial link 33 to a sorter 34. The format of the coincidence data packet may be, for example, a thirty-two bit data stream which includes, among other things, a pair of digital numbers that precisely identify the locations of the two detector crystals 21 that detected the event.

The sorter 34, which may include a CPU and which forms part of an image reconstruction processor 40, receives the coincidence data packets from the coincidence detector 32. The function of the sorter 34 is to receive the coincidence data packets and allocate sinogram memory for the storage of the coincidence data. The set of all projection rays that point in the same direction ($\theta$) and pass through the scanner's field of view is a complete projection, or "view", which makes a set of sinogram. The distance (R) between a particular projection ray and the center of the field of view locates that projection ray within the view. As shown in FIG. 5, for example, an event 50' occurs along a projection ray 51' which is located in a view at the projection angle $\theta$ and the distance R. The sorter 34 counts all of the events that occur on this projection ray (R, $\theta$) during the scan by sorting out the coincidence data packets that indicate an event at the detector crystals 21 lying on the projection ray. During an emission scan, the coincidence counts are organized in memory 43, for example as a set of two-dimensional array, one for each axial image, and each having as one of its dimensions the projection angle $\theta$ and the other dimension the distance R. This $\theta$ by R map of the measured events may be referred to as sinogram array 48. The sorter 34 may also organize the coincidence events into other data formats. In a projection plane format, for example, other variables may be used to define coincidence events which are detected by pairs of detector crystals 21 in non-adjacent detector rings.

Coincidence events occur at random and the sorter 34 determines the $\theta$ and R values from the two crystal addresses in each coincidence data packet and increments the count of the corresponding sinogram array element. At the completion of the emission scan, the sinogram array 48 stores the total number of annihilation events which occurred along each ray. The array processor 45 reconstructs an image from the data in the sinogram array 48. First, however, a number of corrections may be made to the acquired data to correct for measurement errors such as those caused by attenuation of annihilation photons by the patient, detector gain non-uniformities, random coincidences, and integrator dead time. Each row of the corrected sinogram array is then Fourier transformed by the array processor 45 and multiplied by a one-dimensional filter array. The filtered data is then inverse Fourier transformed, and each array element is back projected to form the image array 46. The image CPU 42 may either store the image array data or output the data to the operator work station 15. Alternatively, the image array 46 may be generated by an iterative image reconstruction algorithm run by the array processor 45 and/or the image CPU 42.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuitry capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A method comprising:
    acquiring scan data for an object to be imaged using an imaging scanner;
    reconstructing a display image, with one or more processors, using the scan data;
    determining, with the one or more processors, one or more aspects of a quantitation imaging algorithm for generating a quantitation image, wherein the one or more aspects of the quantitation imaging algorithm are selected to optimize a quantitation figure of merit for lesion quantitation;
    reconstructing a quantitation image, with the one or more processors, using the scan data and the quantitation imaging algorithm;
    displaying, on a display device, the display image;
    determining a region of interest in the display image;
    determining, for the region of interest, a lesion quantitation value using a corresponding region of interest of the quantitation image; and
    displaying, on the display device, the lesion quantitation value.

2. The method of claim 1, wherein the quantitation imaging algorithm is a penalized-likelihood image reconstruction algorithm configured to be used in conjunction with imaging, wherein the one or more aspects comprises at least one of a penalty function type, a penalty strength value or a penalty parameter value, and wherein the one or more aspects are determined based on at least one of a scanner geometry, a data acquisition protocol, a location of a lesion feature to be quantified in the object, an aggregate certainty value, a size of the lesion feature to be quantified, or a scan duration.

3. The method of claim 1, wherein the one or more aspects of the quantitation imaging algorithm are determined using at least one of a background activity, a size of a lesion feature, or a contrast of the lesion feature.

4. The method of claim 1, wherein the quantitation figure of merit for lesion quantitation includes at least one of a mean square error, a bias, a signal-to-noise ratio, a contrast recovery coefficient, or a recovery coefficient.

5. The method of claim 1, wherein the quantitation figure of merit is optimized using a look-up table.

6. The method of claim 1, wherein the quantitation figure of merit is optimized using hybrid lesion insertion.

7. The method of claim 1, further comprising:
    determining, with the one or more processors, one or more aspects of a display imaging algorithm for generating the display image, wherein the display imaging algorithm is a penalized-likelihood image reconstruction algorithm configured to be used in conjunction with imaging, wherein the one or more aspects of the display imaging algorithm comprises at least one of a penalty function type, a penalty strength value or a penalty parameter value, wherein the one or more aspects of the display imaging algorithm are selected to optimize an imaging figure of merit for at least one of lesion detection or visual image quality, wherein the one or more aspects are determined based on at least one of a scanner geometry, a data acquisition protocol, a location of a lesion feature, an aggregate certainty value, a size of the lesion feature, or a scan duration;

wherein reconstructing the display image comprises using the display imaging algorithm.

8. The method of claim 7, wherein the imaging figure of merit comprises at least one of a signal-to-noise ratio, a lesion detectability index, or an area under a receiver operating characteristic curve.

9. The method of claim 7, wherein the imaging figure of merit comprises a subjective image quality score.

10. The method of claim 7, wherein the imaging figure of merit is optimized using a look-up table.

11. The method of claim 7, wherein the imaging figure of merit is optimized using hybrid lesion insertion.

12. A tangible and non-transitory computer readable medium comprising one or more software modules configured to direct one or more processors to:
    acquire scan data for an object to be imaged using an imaging scanner;
    reconstruct a display image, with one or more processors, using the scan data;
    determine one or more aspects of a quantitation imaging algorithm for generating a quantitation image, wherein the one or more aspects of the quantitation imaging algorithm are selected to optimize a quantitation figure of merit for lesion quantitation;
    reconstruct a quantitation image, with the one or more processors, using the scan data and the quantitation imaging algorithm;
    display, on a display device, the display image;
    determine a region of interest in the display image;
    determine, for the region of interest, a lesion quantitation value using a corresponding region of interest of the quantitation image; and
    display, on the display device, the lesion quantitation value.

13. The tangible and non-transitory computer readable medium of claim 12, wherein the quantitation imaging algorithm is a penalized-likelihood image reconstruction algorithm configured to be used in conjunction with imaging, wherein the one or more aspects comprises at least one of a penalty function type, a penalty strength value or a penalty parameter value, and wherein the one or more aspects are determined based on at least one of a scanner geometry, a data acquisition protocol, a location of a lesion feature to be quantified in the object, an aggregate certainty value, a size of the lesion feature to be quantified, or a scan duration.

14. The tangible and non-transitory computer readable medium of claim 12, wherein the one or more software modules are further configured to direct the one or more processors to:
    determine one or more aspects of a display imaging algorithm for generating the display image, wherein the display imaging algorithm is a penalized-likelihood image reconstruction algorithm configured to be used in conjunction with imaging, wherein the one or more aspects of the display imaging algorithm comprises at least one of a penalty function type, a penalty strength value or a penalty parameter value, wherein the one or more aspects of the display imaging algorithm are selected to optimize an imaging figure of merit for at least one of visual image quality or lesion detection, wherein the one or more aspects are determined based on at least one of a scanner geometry, a data acquisition protocol, a location of a lesion feature, an aggregate certainty value, a size of the lesion feature, or a scan duration;
    wherein reconstructing the display image comprises using the display imaging algorithm.

15. A medical imaging detection system comprising:
    a detector unit configured to generate scan data;
    a display device operably coupled to the detector unit; and
    at least one processor operably coupled to the detector unit and the display device, the at least one processor configured to receive the scan data from the detector unit, the at least one processor configured to:
        determine one or more aspects of a quantitation imaging algorithm for generating a quantitation image, wherein the one or more aspects of the quantitation imaging algorithm are selected to optimize a quantitation figure of merit for lesion quantitation;
        reconstruct a display image, with the one or more processors, using the scan data;
        reconstruct a quantitation image, with the one or more processors, using the scan data and the quantitation imaging algorithm;
        display, using the display device, the display image;
        determine a region of interest in the display image;
        determine, for the region of interest, a lesion quantitation value using a corresponding region of interest of the quantitation image; and
        display, on the display device, the lesion quantitation value.

16. The system of claim 15, wherein the quantitation imaging algorithm is a penalized-likelihood image reconstruction algorithm configured to be used in conjunction with imaging, and wherein the one or more aspects comprises at least one of a penalty function type, a penalty strength value or a penalty parameter value, and wherein the one or more aspects are determined based on at least one of a scanner geometry, a data acquisition protocol, a location of a lesion feature to be quantified in the object, an aggregate certainty value, a size of the lesion feature to be quantified, or a scan duration.

17. The system of claim 15, wherein the quantitation figure of merit for lesion quantitation includes at least one of a mean square error, a bias, a signal-to-noise ratio, a contrast recovery coefficient, or a recovery coefficient.

18. The system of claim 15, wherein the at least one processor is further configured to:
    determine one or more aspects of a display imaging algorithm for generating the display image, wherein the display imaging algorithm is a penalized-likelihood image reconstruction algorithm configured to be used in conjunction with imaging, wherein the one or more aspects of the display imaging algorithm comprises at least one of a penalty function type, a penalty strength value or a penalty parameter value, wherein the one or more aspects of the display imaging algorithm are selected to optimize an imaging figure of merit for lesion detection, wherein the one or more aspects are determined based on at least one of a scanner geometry, a data acquisition protocol, a location of a lesion feature, an aggregate certainty value, a size of the lesion feature, or a scan duration;
    wherein reconstructing the display image comprises using the display imaging algorithm.

19. The system of claim 18, wherein the imaging figure of merit comprises at least one of a signal-to-noise ratio, a lesion detectability index, or an area under a receiver operating characteristic curve.

20. The system of claim 15, wherein the at least one processor is further configured to:

determine one or more aspects of a display imaging algorithm for generating the display image, wherein the display imaging algorithm is a penalized-likelihood image reconstruction algorithm configured to be used in conjunction with imaging, wherein the one or more aspects of the display imaging algorithm comprises at least one of a penalty function type, a penalty strength value or a penalty parameter value, wherein the one or more aspects of the display imaging algorithm are selected to optimize an imaging figure of merit for visual image quality, wherein the one or more aspects are determined based on at least one of a scanner geometry, a data acquisition protocol, a location of a lesion feature, an aggregate certainty value, a size of the lesion feature, or a scan duration;

wherein reconstructing the display image comprises using the display imaging algorithm.

* * * * *